United States Patent
Wolters et al.

(10) Patent No.: US 9,523,110 B2
(45) Date of Patent: Dec. 20, 2016

(54) CULTURE CONTAINERS WITH INTERNAL TOP COATING OVER GAS BARRIER COATING AND ASSOCIATED METHODS

(71) Applicant: bioMèrieux, Inc., Durham, NC (US)

(72) Inventors: Weihua Sonya Wolters, Raleigh, NC (US); Stanley Michael Philipak, Augusta, MO (US)

(73) Assignee: bioMerieux, Inc., Durham, NC (US)

( * ) Notice: Subject to any disclaimer, the term of this patent is extended or adjusted under 35 U.S.C. 154(b) by 94 days.

(21) Appl. No.: 13/789,940

(22) Filed: Mar. 8, 2013

(65) Prior Publication Data

US 2014/0234950 A1 Aug. 21, 2014

Related U.S. Application Data

(60) Provisional application No. 61/765,272, filed on Feb. 15, 2013.

(51) Int. Cl.
| | | |
|---|---|---|
| *C12M 3/00* | (2006.01) | |
| *C12M 1/34* | (2006.01) | |
| *C12Q 1/04* | (2006.01) | |
| *C12M 1/24* | (2006.01) | |
| *C12M 1/00* | (2006.01) | |

(52) U.S. Cl.
CPC .............. *C12Q 1/04* (2013.01); *C12M 23/08* (2013.01); *C12M 23/20* (2013.01)

(58) Field of Classification Search
CPC ........... C12Q 1/04; C12M 23/08; C12M 23/20
USPC .................................................... 435/287.9
See application file for complete search history.

(56) References Cited

U.S. PATENT DOCUMENTS

| | | | |
|---|---|---|---|
| 4,528,235 A | 7/1985 | Sacks et al. | |
| 4,536,425 A | 8/1985 | Hekal | |
| 4,584,823 A | 4/1986 | Nagel | |
| 4,827,944 A | 5/1989 | Nugent | |
| 4,911,218 A | 3/1990 | Patitsas | |

(Continued)

FOREIGN PATENT DOCUMENTS

| | | |
|---|---|---|
| WO | WO93/04118 | 3/1993 |
| WO | WO94/26874 | 11/1994 |

(Continued)

OTHER PUBLICATIONS

Gruniger et al., Influence of Defects in SiOx Thin Films on Their Barrier Properties, Thin Solid Films, vol. 459, No. 1-2, pp. 308-312, 2004.*

(Continued)

*Primary Examiner* — Nathan Bowers
(74) *Attorney, Agent, or Firm* — Myers Bigel, P.A.

(57) ABSTRACT

A container for culturing a test sample includes a molded monolithic single layer polymeric container body having an upwardly extending, visually transmissive wall with an inner surface and a wall thickness that is between about 0.2 mm and 10 mm. The container also has a thin gas barrier coating comprising silica on the inner surface of the sealed container body and an internal top coating on the gas barrier coating. The gas barrier and top coating are visually transmissive (after curing). The container includes a cap sealably attached to the container body. The sealed container has an oxygen transmission rate (OTR) after autoclaving and aging that is between about 0.0001 to about 0.04 (cc/package/day/atm).

18 Claims, 6 Drawing Sheets

(56) References Cited

U.S. PATENT DOCUMENTS

| | | | |
|---|---|---|---|
| 4,945,060 A | 7/1990 | Turner et al. | |
| 4,960,639 A | 10/1990 | Oda et al. | |
| 4,983,432 A | 1/1991 | Bissot | |
| 4,995,519 A | 2/1991 | Rose et al. | |
| 5,000,804 A | 3/1991 | Nugent | |
| 5,049,609 A | 9/1991 | Patitsas | |
| 5,090,581 A | 2/1992 | Rose et al. | |
| 5,091,467 A | 2/1992 | Beers | |
| 5,094,955 A | 3/1992 | Calandra et al. | |
| 5,162,229 A | 11/1992 | Thorpe et al. | |
| 5,164,796 A | 11/1992 | Di Guiseppi et al. | |
| 5,217,876 A | 6/1993 | Turner et al. | |
| 5,356,052 A | 10/1994 | Poynter | |
| 5,472,753 A | 12/1995 | Farha | |
| 5,718,967 A * | 2/1998 | Hu et al. | 428/216 |
| 5,770,394 A | 6/1998 | Berndt | |
| 5,795,773 A | 8/1998 | Read et al. | |
| 5,856,175 A | 1/1999 | Thorpe et al. | |
| 5,860,329 A | 1/1999 | Day | |
| 5,908,676 A | 6/1999 | Otaki et al. | |
| 5,968,620 A * | 10/1999 | Harvey et al. | 428/35.9 |
| 6,123,211 A | 9/2000 | Rashid et al. | |
| 6,383,166 B1 | 5/2002 | Farris | |
| 6,709,857 B2 | 3/2004 | Bachur, Jr. | |
| 6,860,405 B1 | 3/2005 | Poynter | |
| 7,028,862 B2 | 4/2006 | Poynter | |
| 7,078,453 B1 | 7/2006 | Feeney et al. | |
| 7,119,138 B1 | 10/2006 | Feeney et al. | |
| 7,211,430 B2 | 5/2007 | Schwarz et al. | |
| 7,473,729 B2 | 1/2009 | Feeney et al. | |
| 7,803,305 B2 | 9/2010 | Ahern et al. | |
| 7,985,188 B2 | 7/2011 | Felts et al. | |
| 8,144,199 B2 | 3/2012 | Takenaka et al. | |
| 2003/0175465 A1 | 9/2003 | Watanabe et al. | |
| 2003/0215652 A1 | 11/2003 | O'Connor | |
| 2004/0101955 A1 | 5/2004 | Whitley | |
| 2006/0110615 A1 | 5/2006 | Karim et al. | |
| 2007/0213446 A1 | 9/2007 | Feeney et al. | |
| 2008/0014429 A1 | 1/2008 | Su et al. | |
| 2008/0131707 A1 | 6/2008 | Feeney et al. | |
| 2009/0133748 A1 | 5/2009 | Sharma | |
| 2009/0162587 A1 | 6/2009 | Wilkinson et al. | |
| 2009/0285722 A1 | 11/2009 | Soskey et al. | |
| 2010/0068755 A1 | 3/2010 | Walsh et al. | |
| 2011/0081714 A1 | 4/2011 | Wilson et al. | |
| 2011/0081715 A1 | 4/2011 | Robinson et al. | |
| 2011/0124028 A1 | 5/2011 | Robinson et al. | |
| 2011/0186537 A1 | 8/2011 | Rodriguez San Juan et al. | |
| 2011/0252899 A1 | 10/2011 | Felts et al. | |
| 2012/0021455 A1 | 1/2012 | Clay | |
| 2012/0123345 A1 * | 5/2012 | Felts | A61M 5/3129 604/187 |

FOREIGN PATENT DOCUMENTS

| | | |
|---|---|---|
| WO | WO2011/014429 | 2/2011 |
| WO | WO2011/016838 | 2/2011 |
| WO | WO2011/041471 | 4/2011 |

OTHER PUBLICATIONS

Blow molding, Packaging technology, http://packaging-technology.org/35-blow-molding.html, Jan. 31, 2012, 26 pages, printed from the internet Sep. 6, 2012.

Guidance for Industry, Sterile Drug Products Produced by Aseptic Processing—Current Good Manufacturing Practice, Pharmaceutical CGMPs, U.S. Department of Health and Human Services, Food and Drug Administration, Center for Drug Evaluation and Research (CDER), Center for Biologics Evaluation and Research (CBER), Office of Regulatory Affairs (ORA), Sep. 2004, 19 pages.

Mrkic et al., Effect of Temperature and Mechanical Stress on Barrier Properties of Polymeric Films Used for Food Packaging, Journal of Plastic Film & Sheeting, 2007, pp. 239-256, vol. 23, No. 3.

Siracusa, Food Packaging Permeability Behavior: A Report, International Journal of Polymer Science, 2012, 11 pages, http//dx.org/10.1155/2012/302029, printed from the internet Apr. 20, 2015.

International Search Report and Written Opinion for corresponding PCT Application No. PCTUS2014/015575, dated May 19, 2014, 8 pages.

* cited by examiner

CULTURE CONTAINERS WITH INTERNAL TOP COATING OVER GAS BARRIER COATING AND ASSOCIATED METHODS

RELATED APPLICATIONS

This application claims the benefit of and priority to U.S. Provisional Application Ser. No. 61/765,272 filed Feb. 15, 2013, the contents of which are hereby incorporated by reference as if recited in full herein.

FIELD OF THE INVENTION

This invention relates to economic containers that are particularly suitable for culturing biosamples.

BACKGROUND OF THE INVENTION

Bottles for collection or culturing of blood and other biological or industrial samples are known in the art. See, e.g., U.S. Pat. Nos. 4,945,060; 5,094,955; 5,860,329; 4,827,944; 5,000,804; 7,211,430 and U.S. Patent Publication No. 2005/0037165.

Sample culture bottles or containers typically contain a headspace gas composition to facilitate the recovery of organisms. The blood culture container is made of a suitable gas-impermeable material to ensure that the integrity of the gas composition in the headspace of the bottle is maintained throughout the shelf life of the bottle. For typical analysis, the container should ideally remain visually optically transmissive, typically transparent, through its life to allow for one or more of (i) manual or electronic observation of the contents of the container, (ii) measuring fill level when using the container, (iii) visual observation of contents after culturing or growth, and (iv) a reading of an internal sensor in the container that detects microbial growth.

Several types of blood culture bottles have been used that limit gas diffusion into or out of the bottle. One type is a glass vial with an elastomeric seal. The glass vial itself provides the gas barrier. However, if a glass vial is dropped it may break, exposing the user to glass shards and, potentially, biologically hazardous materials. Furthermore, the nature of glass manufacturing can leave undetectable microcracks in the glass, which under the pressure of microbial growth in the vial can lead to bottle rupturing, and, again, exposure to biohazardous materials.

A second type of blood culture bottle is a multi-layer plastic vial. See, e.g., U.S. Pat. No. 6,123,211 and U.S. Patent Publication No. 2005/0037165. The multi-layer plastic vial is fabricated from two plastic materials that each serve different functions. For example, the interior and exterior layers of the vials can be produced from polycarbonate, which offers the strength and rigidity required for product use. Likewise, polycarbonate can withstand higher temperatures required for autoclave of the product during manufacture and remains transparent. However, the polycarbonate does not provide a sufficient gas barrier. The middle material layer can be fabricated from nylon, which provides the required gas barrier. The nylon, by itself, does not have the necessary rigidity and strength to withstand the autoclave temperatures required during the manufacture of blood culture bottles, since it would not remain transparent if exposed to moisture or autoclaved. The multilayer plastic vial offers advantages over the glass vials. However, multi-layer plastic vials are produced with relatively complex manufacturing methods and the vials are consequently relatively expensive.

More recently, single layer plastic bottles have been proposed which employ an autoclave or bottle sterilization process to provide the necessary cleanliness/sterility. See, e.g., U.S. Patent Publication No. 2011/0081714, the contents of which are incorporated by reference as if recited in full herein.

Despite the above, there remains a need for cost-effective test sample containers and fabrication methods.

SUMMARY OF EMBODIMENTS OF THE INVENTION

Embodiments of the invention are directed to biosample culture bottles with internal top coatings that can inhibit degradation of gas barrier coatings.

The culture bottles can be monolithic single layer plastic culture bottles with an internal top coating over an underlying gas barrier coating.

Embodiments of the invention provide containers for culturing a test sample. The containers include a molded monolithic single layer polymeric container body having an upwardly extending, visually transmissive wall with an inner surface and a wall thickness that is between about 0.2 mm and 10 mm. The containers also have a thin gas barrier coating comprising silica on the inner surface of the sealed container body and an internal top coating on the gas barrier coating. The gas barrier and top coating are visually transmissive. The container includes a cap sealably attached to the container body. The sealed container has an oxygen transmission rate (OTR) after manufacturing and throughout its shelf life between about 0.0001 to about 0.04 (cc/package/day/atm, 20° C./40% RH).

The containers can include an LES (Liquid Emulsion Silicone) sensor on the top coating in a bottom of the container body, and cell culture media in the container.

The containers can include an external coating on the container body, wherein the external coating can be formed of a material corresponding to the top coating.

The top coating can be poly-para-xylylene.

The top coating can include carbon.

The top coating can include acetylene.

The container body can have a wall thickness of between about 1-5 mm (on average). The gas barrier coating can have a thickness of between about 10-1000 nm (on average) and the top coating can have a thickness between about 10 nm to about 100 microns (on average).

The container body can have a wall thickness that is between 1-2 mm, on average.

The container body can be a transparent polycarbonate body or a transparent cyclic olefin copolymer body.

The container body can be devoid of an external coating.

Other embodiments are directed to evacuated blood culture sample containers. The containers include: (a) an elongate molded monolithic single layer polymeric container body having an upwardly extending, visually transmissive wall with a wall thickness that is between about 0.2 and 10 mm; (b) a colorimetric sensor in the container body; (c) organism growth media in the container body; (d) an elastomeric stopper and a crimp seal attached to the container body; (e) a thin visually transmissive gas barrier coating on the inner surface of the sealed container body; and (f) a thin top coating on the gas barrier coating. After manufacturing and throughout its shelf life, the sealed container with the internal gas barrier coating and top coating has an oxygen transmission rate that is between about 0.0001 and 0.04 (cc/container/day/atm air, 20° C./40% RH), on average.

The colorimetric sensor can include an LES sensor on the top coating in a bottom of the container body.

The organism growth media can include non-acidic cell culture media in the container.

The gas barrier coating can include silica and the top coating can include poly-para-xylylene.

The gas barrier coating can include silica and the top coating can include carbon.

The gas barrier coating can include silica and the top coating can include acetylene.

The container body can have a wall thickness of between about 0.2-10 mm (on average), typically 1-5 mm (on average). The gas barrier coating can have a thickness of between about 10-1000 nm (on average) and the top coating can have a thickness between about 10 nm-100 microns (on average).

The container body can have a wall thickness that is between 1-2 mm, on average, and the container body can be a transparent polycarbonate body or a transparent cyclic olefin copolymer body.

The container body can have an upper portion with a shoulder that merges into a narrow neck and the sealed container can include a metallic cap extending over the stopper, crimped to attach to an upper portion of the container neck.

Still other embodiments are directed to methods of manufacturing a test sample culture device. The methods include: (a) molding or providing a molded single layer plastic container body having an interior surface and an exterior surface with a wall thickness of between about 0.2 mm to about 10 mm (average); (b) coating the interior surface of the container body with a gas barrier coating comprising silica that defines a visually transmissive thin gas barrier layer; (c) coating the gas barrier layer with an over-layer of a different material to define a visually transmissive thin top coat; then (d) adding a growth media to the container body; (e) adding a defined headspace gas composition to the bottle; and (f) placing a cap on the container body to seal the container shut.

The colorimetric sensor material can include Liquid Emulsion Silicone (LES).

The culture container can be a blood sample container for culturing microbes in a blood sample.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

DETAILED DESCRIPTION OF EMBODIMENTS OF THE INVENTION

Figure 1:
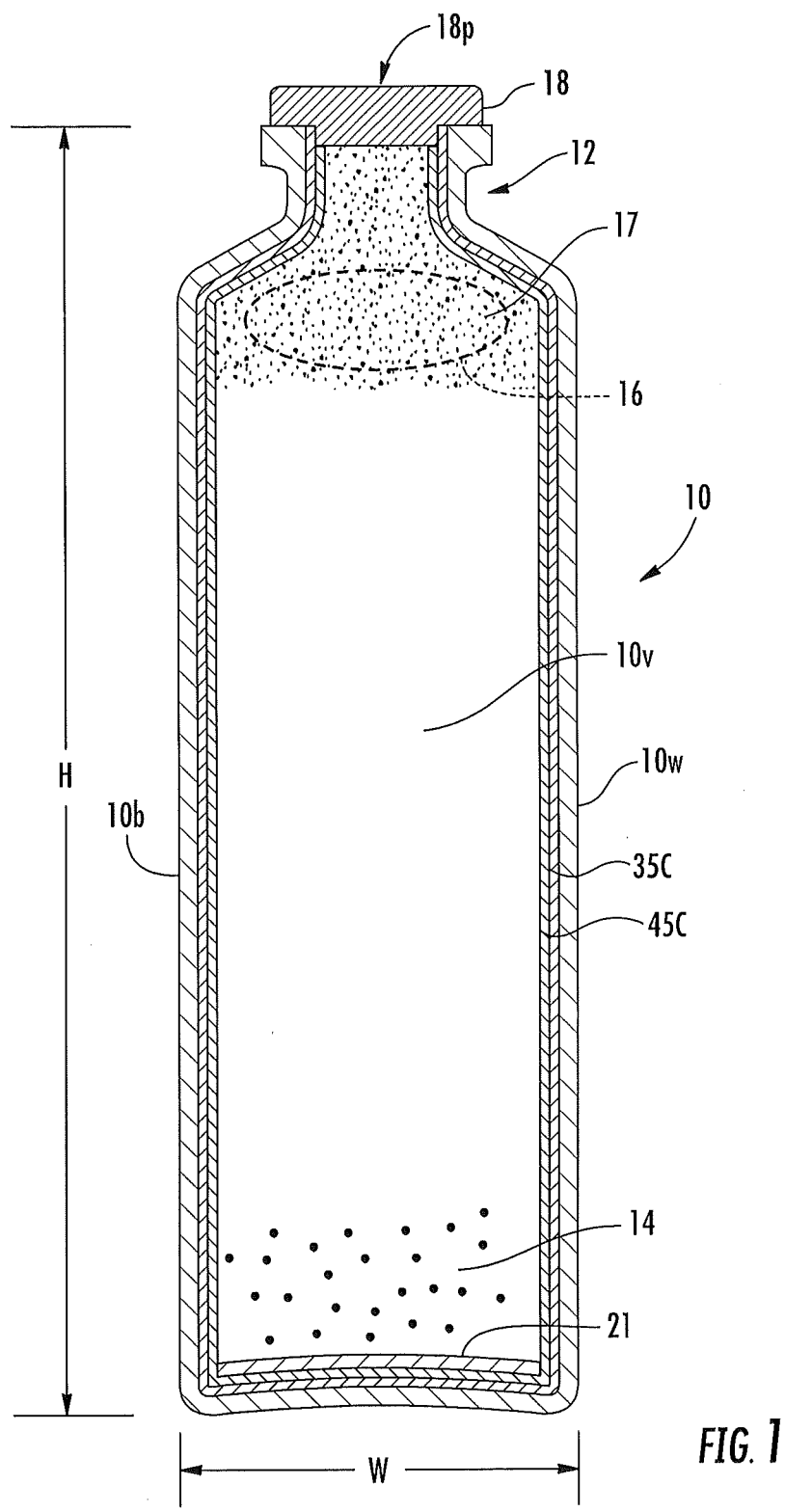
FIG. 1 is a sectional view of an exemplary culture container according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

The term "sample" refers to a target material undergoing testing or analysis for content. The sample can be a food sample, an environmental sample (water, air, soil, etc.) or a biosample. The testing can be for quality control of food produced in a commercial manufacturing facility, for the EPA (Environmental Protection Agency of the U.S. Government), for environmental toxins or hazardous materials that are man-made, intentional or not, or medical (clinical diagnostic) purposes.

The term "biosample" refers to human or animal tissue, blood, blood plasma or serum, blood fractions, joint fluid, urine, semen, saliva, feces, cerebrospinal fluid, gastric contents, vaginal secretions, tissue homogenates, bone marrow aspirates, bone homogenates, sputum or lavages, aspirates, swabs and swab rinsates, blood products (e.g., platelets, serum, plasma, white blood cell fractions, etc.), donor organ or tissue samples, and the like. In one embodiment, the biological sample tested is a blood sample, urine, cerebral spinal fluid, lavages, mucus or other solid or liquid samples for analysis which may have microbes, microorganisms, toxins and/or cellular material or other constituents of interest. Embodiments of the invention may be suitable for veterinarian use, medical human use or research for human and/or with laboratory animals.

In general, the containers can be used for any known test sample (e.g., a biological sample or specimen). For example, the test sample can be a clinical or non-clinical sample suspected of containing one or more microbial agents. Other samples that may be tested include, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, and fruit) and biowarfare samples.

The term "sterile" and derivatives thereof mean that the noted device or material meets or exceeds defined (e.g., food or medical) guidelines of sterility so as to be substantially (if not totally) free of contaminants for at least a defined shelf life so as to be suitable for intended uses, e.g., clinical, health, or consumer product testing for the presence of toxins, microbes, microorganisms or other target constituents in a sample undergoing analysis. The sample can undergo analysis while held in the container. The sample may be transferred after transport and/or culturing in the container for analysis.

The term "aseptic" is used interchangeably with the word "sterile". In some embodiments, the aseptic processing or fabrication complies with GMP (Good Manufacturing Practice) industry guidelines such as those associated with Guidance for Industry—Sterile Drug Products Produced by Aseptic Processing—Current Good Manufacturing Practice, U.S. Department of Health and Human Services Food and Drug Administration, September 2004.

The term "parison" refers to a preform of material that is subsequently blown into a shape defined by an enclosed mold ("blow-molding") with pressurized gas using conventional blow molding processes (typically extrusion-based methods) as is well known to those of skill in the art.

The term "automatic" means that the operation can be carried out using automated electromechanical equipment, rather than with manual labor.

The term "substantially impermeable" means that the sealed container has low permeability, e.g., an oxygen transmission rate (cubic centimeter/day/atm air) that is between about 0.00001 to about 0.1 cc/day/atm. As described below, sealed containers contemplated by embodiments of the invention are substantially impermeable. The sealed containers 10 typically have oxygen transmission rates (cubic centimeter/day/atm air) that are between 0.0001 to about 0.01 or 0.04 after manufacturing and throughout at least a one year shelf life, typically a 1-2 year shelf life. The test conditions can be at 1 atm, a relative humidity ("RH %") that is 40% and a room temperature that is 20 degrees C. The term "day" means 24 hours. The oxygen transmission rate can be determined using MOCON Oxytran 2/61 Oxygen Permeability Instrument via ASTM F-1307 or other suitable instruments and protocols. An accelerated age test can be carried out at 80 degrees C. for seven (7) days. The age test is typically after the container has been filled with sensor and growth media, sealed and autoclaved.

The term "thin" with reference to a coating refers to a thickness of between about 1 nm to about 1000 microns (on average), typically between about 1 nm-100 microns (on average), more typically between about 10 nm to about 100 microns (on average), such as (on average) about 10 nm, about 15 nm, about 20 nm, about 25 nm, about 30 nm, about 35 nm, about 40 nm, about 45 nm, about 50 nm, about 55 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm about 200 nm, about 210 nm, about 220 nm, about 230 nm, about 240 nm, about 250 nm, about 260 nm, about 270 nm, about 280 nm, about 290 nm, about 300 nm, about 325 nm, about 350 nm, about 375 nm, about 400, nm, about 425 nm, about 450 nm, about 475 nm, about 500 nm, about 550 nm, about 600 nm, about 650 nm, about 700 nm, about 750 nm, about 800 nm, about 850 nm, about 900 nm, about 1000 nm, about 2 microns, about 3 microns, about 4 microns, about 5 microns, about 10 microns, 20 microns, about 25 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, and about 100 microns.

The term "draw volume" refers to draw of deionized water as is known to those of skill in the art.

The term "aging" refers to the change that a product undergoes throughout the shelf life. An accelerated aging test uses an elevated temperature and shorter time to assess the product performance through its shelf life. In general, Arrhenius equation $k=A\,e\,(-Ea/RT)$ applies to a product aging process, where k is the aging rate, A is the pre-exponential factor, Ea is the activation energy for the aging process, and R is the universal gas constant which is 8.31 J/mol K. Activation energy determines the temperature dependence of the aging process. Different materials or systems have different activation energies. For accelerated aging studies, since the temperature is elevated, the aging rate increases, therefore a shorter time is needed to assess the product performance.

For a system that the activation energy is not known, a rule of thumb of Arrhenius equation (every ten degree temperature increase correlates to double the reaction rate) is generally used. Normally culture bottles are stored in room temperature of laboratories with an average temperature of 20° C., an 80° C. temperature would possibly accelerate the aging process sixty-four times. A seven day test at 80° C. (e.g., in a temperature controlled incubator or oven) can represent approximately a one year shelf life of containers contemplated by embodiments of the invention. Thus, to assess the OTR performance of a container at a 1 year shelf life, an accelerated aging analysis of seven days at 80° C. can be performed. As is known to those of skill in the art, 80° C. is a typical accelerated aging temperature for products contemplated by embodiments of the invention.

Figure 2:
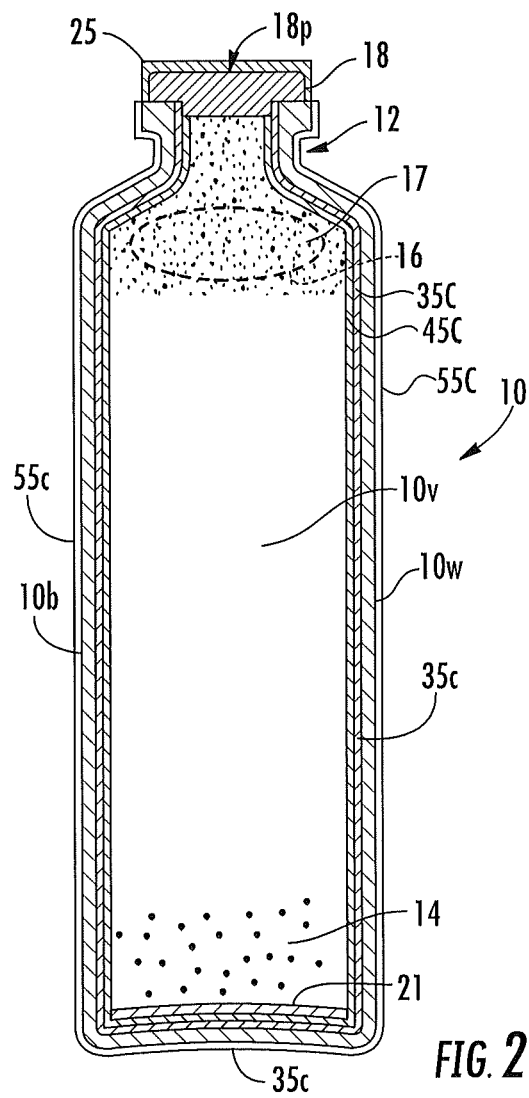
FIG. 2 is a sectional view of an exemplary culture container similar to that shown in FIG. 1, but that also includes an external barrier coating according to embodiments of the present invention.

Turning now to the figures, FIGS. 1 and 2 illustrate an exemplary sample culture container 10. The container 10 can have a body shape in the form of a standard culture bottle (e.g., a blood culture bottle). However, the description of a culture bottle (e.g., a blood culture bottle) is offered by way of example and not limitation. As shown, the containers 10 are elongated containers with an internal volume 10v and an outer wall 10w having an outermost width dimension (W) being less than a height dimension (H). In some embodiments, the height (H) is greater than twice the width (W), e.g., H>2 W. In some embodiments, the containers 10 have tubular bodies with maximum outer diameters between about 1-2 inches and heights of between about 2-5 inches. In some particular embodiments, the containers 10 have an outer diameter of about 1.36 inches (34.6 mm) and a height that is about 4.68 inches (119 mm).

The container 10 may include a bar code label (not shown) for automated reading of patient data and/or test parameters of the content of the container 10. In some embodiments, the top portion of the container 10 can include a narrow portion or neck 12. The container 10 may also include an elastomeric stopper 18 optionally having a self-(re)sealing pierceable material and/or septum 18p.

The container 10 can have a headspace 16 that can accommodate a target (non-air) gas or gas mixture. The gas 17 in the headspace 16 can be introduced into the container 10 during manufacture as will be discussed below. The gases introduced into the container could be oxygen, nitrogen, carbon dioxide, helium, or combination of these gases. The gas could be introduced into the container at a vacuum. The vacuum can be between 3-20 inch Hg, such as about 4.5 inch, about 8 inch, or about 17 inch Hg.

In some embodiments, a cap 25, such as an aluminum or other suitable material can be placed on the top of the container 10 over the stopper 18 as shown in FIG. 2. Typically, the cap 25 is crimped to attach to the upper portion of the container body (e.g., forming a crimp seal over the stopper 18).

In some embodiments, the container 10 may also have an internal sensor 21 (e.g., a Liquid Emulsion Silicone "LES" sensor) formed or placed in the bottom portion of the container 10 for purposes of visual/optic detection of the internal content (e.g., such as via a colorimetric or fluorescent sensor), to detect the presence of microbial or other growth in the container 10. The container 10 can include a body with an optically/visually transmissive material. The body 10b can have a wall 10w that is substantially transparent or sufficiently translucent at the time of testing to allow for visual detection of container content therein.

A variety of sensor technologies are available in the art and may suitable. In some embodiments, the detection unit takes colorimetric measurements as described in the U.S. Pat. Nos. 4,945,060; 5,094,955; 5,162,229; 5,164,796; 5,217,876; 5,795,773; and 5,856,175, which are incorporated by reference as if recited in full herein. A positive container can be identified depending upon these colorimetric measurements, as explained in these patents. Alternatively, detection could also be accomplished using intrinsic fluorescence of the microorganism, and/or detection of changes in the optical scattering of the media (as disclosed, for example, in co-pending U.S. patent application Ser. No. 12/460,607, filed Jul. 22, 2009 and entitled, "Method and System for Detection and/or Characterization of a Biological Particle in a Sample"), which is also incorporated by reference as if recited in full herein. In yet another embodiment, detection can be accomplished by detecting or sensing the generation of volatile organic compounds in the media or headspace of the container.

Exemplary analytical instruments for analyzing the bottles for presence of organisms include U.S. Pat. Nos. 4,945,060; 5,094,955; 6,709,857 and 5,770,394, U.S. Patent Publication 2011/0124028 and PCT Publication WO 94/26874. The contents of these documents are hereby incorporated by reference as if recited in full herein. As described in more detail in U.S. Patent Publication 2011/0124028 incorporated by reference hereinabove, an automated detection system may contain one or more work-flow stations for obtaining one or more measurements, readings, scans and/or images of a specimen container, thereby providing information, such as container type, container lot number, container expiration date, patient information, sample type, test type, fill level, weight measurement, and the like.

The container 10 may further comprise a growth or culture medium 14 for promoting and/or enhancing microbial or microorganism growth. The use of a growth or culture media (or medium) for the cultivation of microorganisms is well known. A suitable growth or culture medium provides the proper nutritional and environmental conditions for growth of microorganisms and should contain all the nutrients required by the microorganism which is to be cultivated in the specimen container 10. The growth media 14 can comprise culture growth media for enhancing or promoting microorganism growth. The media can include a growth media for an aerobic organism or an anaerobic organism.

Figure 3:
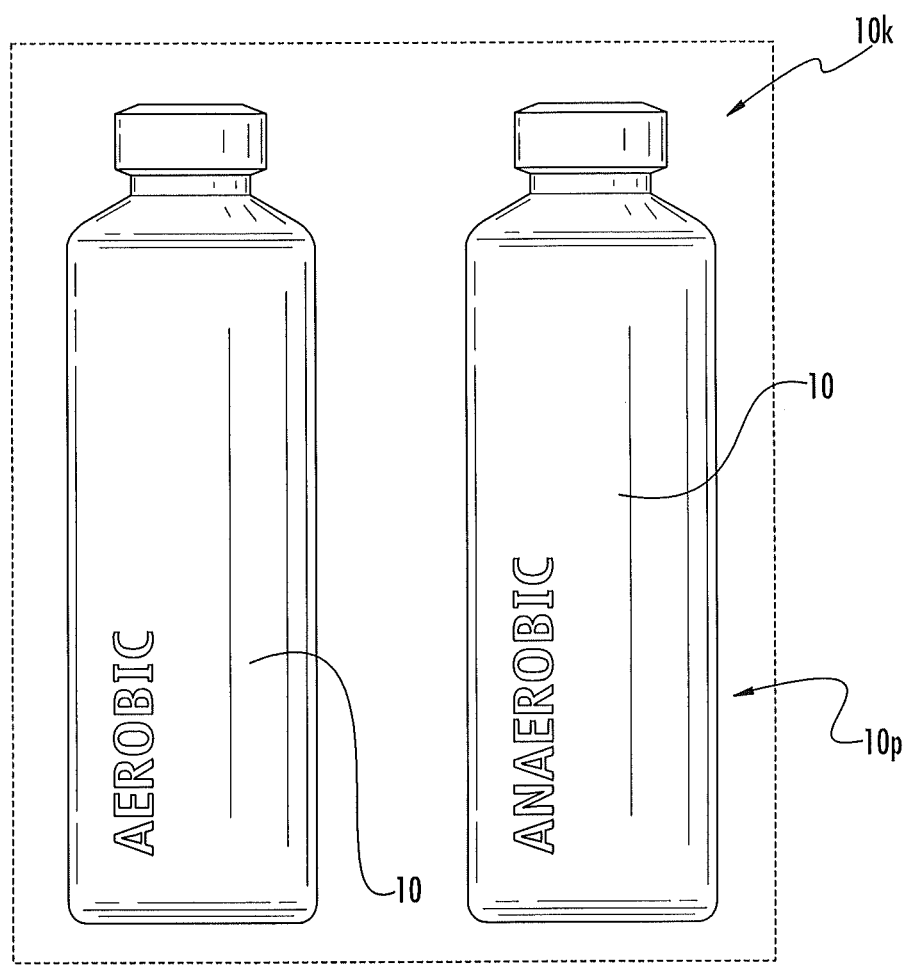
FIG. 3 is a front view of an exemplary kit of sample containers according to embodiments of the present invention.

As shown in FIG. 3, the containers 10 can be provided as a set or kit 10k of at least two containers with one labeled aerobic and one labeled anaerobic. The set or kit 10k may be held in a common package 10p or held separately.

After a sufficient time interval to allow amplification of microorganisms (this time interval varies from species to species), the container 10 can be tested within an automated detection system for evaluating the presence of microbial or microorganism growth. The testing may occur continuously or on a periodic basis so that the container content can be electronically determined as positive for microorganism growth as soon as possible.

The container 10 can include a body 10b that is molded. The body 10b can be a molded polymeric body 10b (e.g., a thermoplastic material body) made from a single layer of polymeric (plastic) monolithic material. The polymer and/or plastic material used to form the container body 10b preferably meets two requirements: (a) it is structurally substantially unaffected (immune to) by high temperatures occurring during autoclaving so that it is able to maintain a rigid or semi-rigid body and (b) the container body is made from a transparent or at least sufficiently optically transmissive material to allow optical reading of a colorimetric sensor in the bottle. Examples of container body materials include, but are not limited to, polycarbonate, polyolefin such as polypropylene (PP), polyethylene (PE), or cyclic olefin (COC), polyester such as polyethylene terephthalate (PET) or polyethylene napthalate (PEN), polyamide (nylon), or other well-known materials in the plastics art. Amorphous plastics such as amorphous nylon exhibit high transparency and may also be suitable. The polymer material can comprise a thermoplastic material. The container body can be formed from for, example, polycarbonate, polyolefin, polyester, polyethylene, cyclic olefin copolymer (COC) and nylon.

The body 10b can be a molded body of a single monolithic layer (e.g., "monolayer") of thermoplastic material that can have a wall thickness between 0.2 mm to about 10 mm, such as about 0.2 mm, about 0.3 mm, about 0.4 mm, about 0.5 mm, about 0.6 mm, about 0.7 mm, about 0.8 mm, about 0.9 mm, about 1 mm, about 1.25 mm, about 1.5 mm, about 1.75 mm, about 2 mm, about 2.5 mm, about 3 mm, about 3.5 mm, about 4 mm, about 4.5 mm, about 5 mm, about 6 mm, about 6.5 mm, about 7 mm, about 7.5 mm, about 8 mm, about 9 mm and about 10 mm. Preferred embodiments use blow-molding for forming the container body. Other types of techniques for manufacture of the container body are also possible.

As shown in FIGS. 1 and 2, the container body 10b includes an internal gas barrier 35c of one or more layers such as one, two or three coating layers of a gas barrier material or materials. The gas barrier coating 35c is substantially gas impermeable and is visually transmissive, typically transparent, in use. The coating 35c can be optically transmissive, typically transparent, after solidifying and/or curing to the inner wall of the container body 10b. The gas barrier coating 35c can have a substantially common thickness (on average) over its entire appended surface or may have a different thickness along different portions of the inner wall.

As also shown in FIG. 2, in some embodiments, the exterior wall of the bottle can also have a gas barrier 55c. The external gas barrier 55c can be the same material as the internal gas barrier 35c. In other embodiments, the external gas barrier 55c, where used, may be a different material gas barrier. The internal and external gas barrier layers 35c, 55c, where both are used, may have the same or different thicknesses (on average) or one may have a greater thickness than the other.

Figure 7:
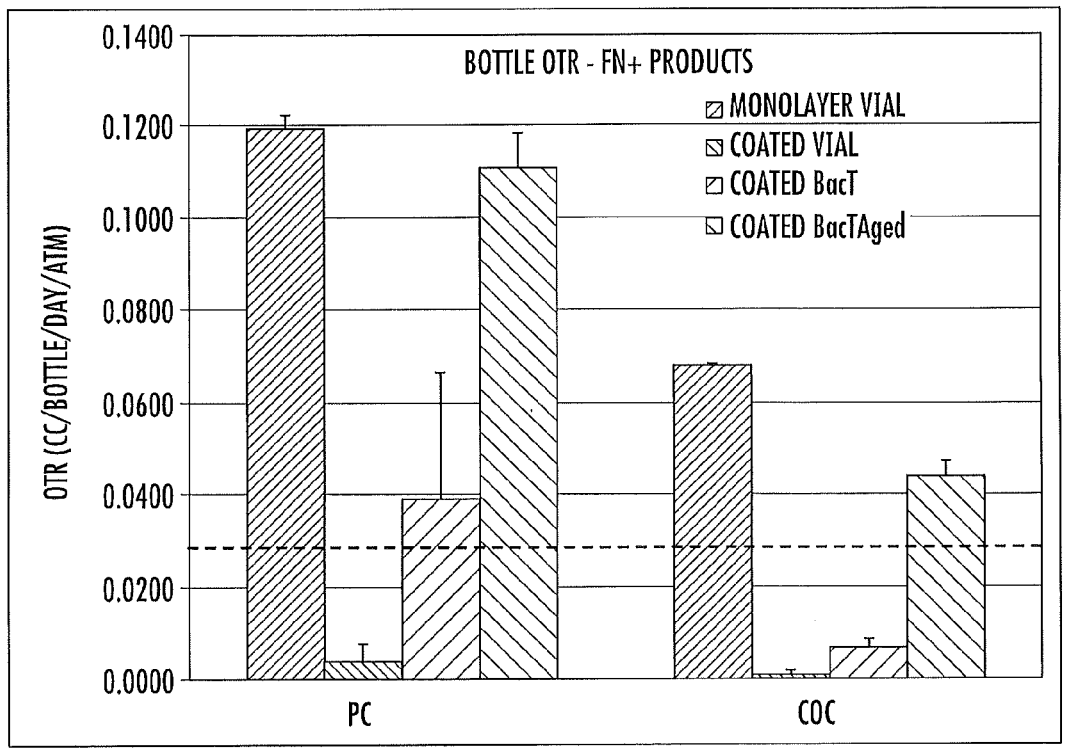
FIG. 7 is a graph of oxygen transmission rates (cc/bottle/day/atm) of various culture containers after manufacturing and after accelerated aging according to embodiments of the present invention.

The gas barrier coating 35c typically comprises silica. Other coatings that provide a gas barrier may also be used, and may include, for example, a metal coating layer, a ceramic coating layer, or a gas barrier plastic coating layer. An internal silica coating was proposed in U.S. Patent Publication No. 2011/081715, the contents of which are hereby incorporated by reference as if recited in full herein. However, it has been discovered that the silica coating can dissolve or degrade over time as shown in FIG. 7. It is believed that the gas barrier loss after manufacturing process (silica coating has direct contact with media at elevated temperature of 121 C) and after an accelerated aging process (the silica coating still has direct contact with media at an elevated temperature of 80 C) was because of the silica coating loss into the media. Silica is relatively stable in an acidic environment while it dissolves at a neutral or high pH environment. The dissolution rate increases significantly with increased temperature or prolonged time, especially with thin layers.

Figure 6:
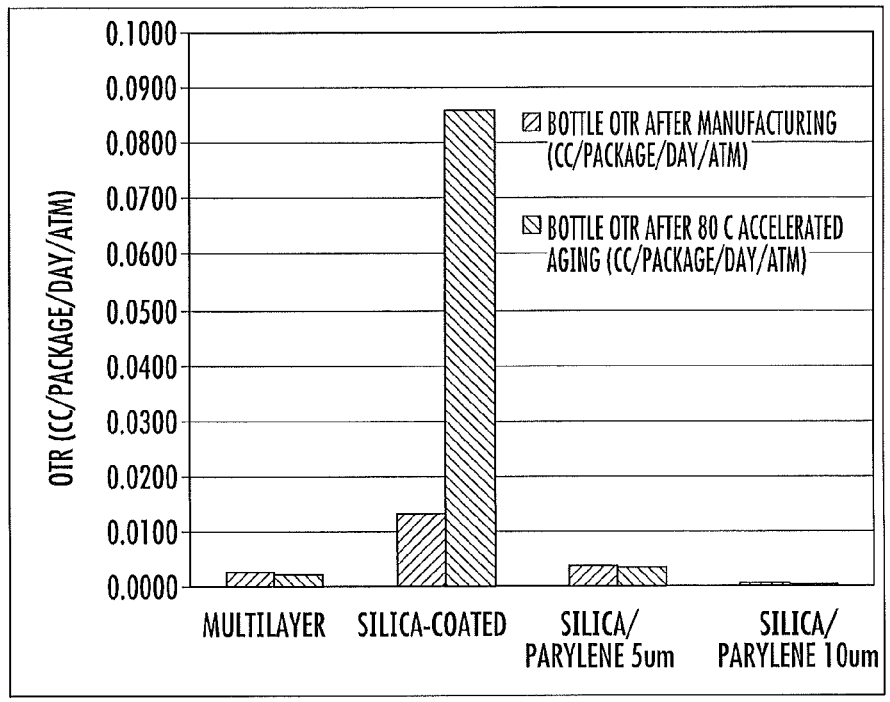
FIG. 6 is a graph of oxygen transmission rates (cc/bottle/day/atm) of different container materials/configurations (associated with FN products).

The present invention describes that, unexpectedly, the addition of an internal top coat 45c over the internal gas barrier coating 35c can protect the gas barrier coating 35c so that after autoclaving and over time, the container 10 retains a suitable OTR (oxygen transmission rate) as shown by FIG. 6 with the silica-coated high OTR after aging compared to the silica with a top coat container OTR. Moreover, unexpectedly, even if the top coat 45c is not a good gas barrier, the addition of the top coat 45c on silica coating 35c not only maintains but further significantly improves the gas barrier of the silica coating 35c.

Examples of top coat materials include, but are not limited to, moisture barrier coatings comprising one or more of Parylene (poly(p-xylylene) polymers including an economical Parylene C material, carbon or acetylene. Parylene is a commercial name for polymers for conformal coatings which belong to a unique chemical family: poly-para-xylylene. In contrast to conventional dip, spray, or flow coatings, Parylene uses gaseous monomers which are polymerized and deposited on substrates.

The top coat 45c could comprise other protective coating materials that retain sufficient optical/visual transmissiveness, post-sterilization and during culturing or incubation. The top coat is not limited to vapor deposition processes or related coatings. For example, the top coat can be a water based coating solution that can be dispersion cured by heat, a liquid coating cured by UV irradiation, or a nanocomposite coating.

The top coat 45c is configured to protect the underlying gas barrier coating 35c to provide a physical shield or barrier to preclude the gas barrier (silica) coating 35c from contacting and/or chemically interacting with contents of the container such as the media so that the container 10 retains sufficient gas barrier properties to provide a low OTR over time, such as after autoclaving and after an accelerated age test.

The internal top coat 45c can be a thin top coat. The thin top coat can typically have a thickness of between about 10 nm to about 100 microns (average), more typically between 10 nm and 10 microns (average), including between 10 nm to 5 microns (average), such as about 10 nm, about 15 nm, about 20 nm, about 30 nm, about 35 nm, about 40 nm, about 45 nm, about 50 nm, about 55 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm about 200 nm, about 210 nm, about 220 nm, about 230 nm, about 240 nm, about 250 nm, about 260 nm, about 270 nm, about 280 nm, about 290 nm, about 300 nm, about 325 nm, about 350 nm, about 375 nm, about 400, nm, about 425 nm, about 450 nm, about 475 nm, about 500 nm, about 550 nm, about 600 nm, about 650 nm, about 700 nm, about 750 nm, about 800 nm, about 850 nm, about 900 nm, about 1000 nm, about 2 microns, about 3 microns, about 4 microns, about 5 microns (all on average).

Figure 4:
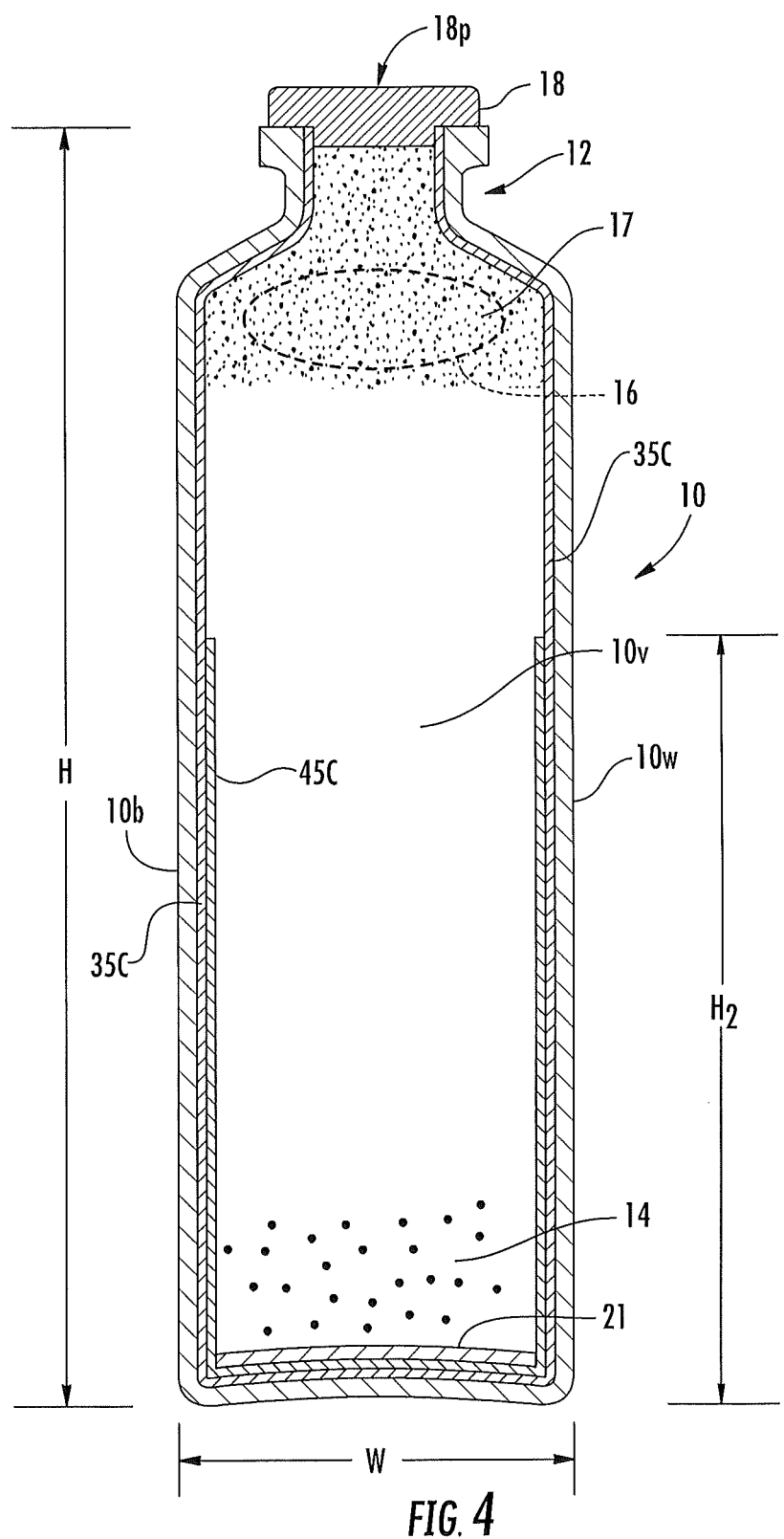
FIG. 4 is a sectional view of an exemplary culture container similar to that shown in FIG. 1, but illustrating a different internal top coat configuration according to embodiments of the present invention.

The top coat 45c can reside over substantially all of the gas barrier coating 35c. In other embodiments, as shown in FIG. 4, the top coat 45c may reside over a subset of the gas barrier coating 35c, e.g., the bottom portion and at least a lower portion of the internal surface (over the gas barrier coating) of a subportion of a height "H2" of the sidewalls 10w, typically covering at least about 80% or extending to a location that is above half the length/height of the container 10.

The interior gas barrier coating 35c can comprise silica $SiO_2$. The silica can be in different forms, such as fumed silica, colloidal silica, silica gel, amorphous silica, and crystalline silica (e.g., quartz, cristobalite, and tridymite). Silica can also be functionalized with different chemical moieties, such as amine-functionalized silica. The silica coating formulation can be organic or inorganic silicon material and/or composite.

For purposes of future evaluation of an oxygen transmission rate (OTR) after autoclaving, the temperature of the autoclaving is about 121 C for 15 minutes with additional time for a ramp up and ramp down program. According to some embodiments, and as will be described further below in the Examples section, the use of an internal top coat layer alone (e.g., Parylene by itself) may not improve the container's oxygen barrier, but when added on top of a silica coating, unexpectedly, the Parylene coating can further improve the container's oxygen barrier status by almost an order of magnitude (at least when top coated with sufficient thickness, e.g., 10 micron thickness, but thinner coatings may also provide suitable benefits).

The glass coating 35c can be introduced by any suitable method, including, for example, thermal spraying, plasma spraying or chemical vapor deposition, and plasma-induced chemical vapor deposition. The gas barrier coating 35c may also be introduced into the parison used to form the container body where blow molding fabrication methods are used. The method may employ high frequency energy in combination with hexamethyl disiloxane in an oxygen-rich environment to result in deposition of silica ($SiO_2$) on the inner surface of the bottle. The top coating 45c can also be introduced by any suitable method, including one or more of the methods described herein for the gas barrier coating 35c.

The container 10, once sealed shut with internal content such as the sensor material 21 and growth media 14, can be sterilized, typically by autoclaving. Autoclaving is currently believed to be the most effective and most efficient means of sterilization. As is well known, autoclaves operate on a time/temperature relationship. Higher temperatures ensure more rapid killing. Some standard autoclave temperature/ pressures employed are 115° C./10 p.s.i., 121° C./15 p.s.i., and 132° C./27 p.s.i., for a suitable time. In some embodiments, the autoclave process can be carried out using a temperature of about 121 degrees C. for about 15 minutes with a heating and cooling ramp cycle.

The container body 10b with the internal gas barrier and top coatings, 35c, 45c, respectively are visually transmissive and substantially impermeable at normal environmental pressures allowing for a suitable shelf life. In some embodiments, the container 10 with the monolithic polymer container body 10b having the internal gas barrier coating 35c and top coat 45c has an oxygen transmission rate (cubic centimeter/day/atm air) that is between 0.0001 to about 0.04, more typically between about 0.0003 to 0.0035 (on average), after autoclaving and an accelerated age test that includes sensor and internal growth media.

In some embodiments, the container 10 has a molded, single layer polymeric wall thickness of about 1.5 mm (nominal). The gas barrier coating 35c can depend on the material(s) used, and can be between 10 nm to about 10 microns. However, in some embodiments, the gas barrier coating is between about 10 nm and 1000 nm (average), such as, for example, about 10 nm, about 15 nm, about 20 nm, about 25 nm, about 30 nm, about 35 nm, about 40 nm, about 45 nm, about 50 nm, about 55 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm about 200 nm, about 210 nm, about 220 nm, about 230 nm, about 240 nm, about 250 nm, about 260 nm, about 270 nm, about 280 nm, about 290 nm, about 300 nm, about 325 nm, about 350 nm, about 375 nm, about 400, nm, about 425 nm, about 450 nm, about 475 nm, about 500 m, about 550 nm, about 600 nm, about 650 nm, about 700 nm, about 750 nm, about 800 nm, about 850 nm, about 900 nm, about 1000 nm, (all on average).

In some particular embodiments, the top coat 45c can have a thickness between 10 nm to 15 microns (on average) such as between about 10 nm to 100 nm (average).

Surface preparations can be carried out and/or adherents such as plasma, flame treatment or primers can be applied to promote coating adhesion prior to applying a respective barrier material 35c or top coat 45c.

It is contemplated that other top coat or gas barrier materials can include polyesters, PVDC, PVOH, PAN, PA, polyamide (PA) polyurethanes, acrylic polymers, polyetheramines, nanocomposites, and metal oxide such as aluminum oxide. The barrier properties of a polymer may be improved by the addition of impermeable-plate like structures such as kaolin, vermiculite, montmorillonite and so forth. See U.S. Pat. Nos. 5,472,753; 4,528,235; 4,536,425; 4,911,218; 4,960,639; 4,983,432; 5,091,467; and 5,049,609; and International Patent Application No. WO93/04118, published Mar. 4, 1993, among others. Other known nanocomposite gas barrier or top coatings which may be suitable are disclosed in the following: U.S. Pat. Nos. 7,078,453; 7,119, 138; 7,473,729; and co-pending U.S. Patent Publication Nos. US2007/0213446; US 2008/0131707; US 2006/

0110615, the disclosures of which are incorporated herein by reference. Other suitable top coat materials 45c may include (if they are able to withstand autoclaving), for example, a laminate film such as a polypropylene film with reprocessed/recycled polyhydroxyamino ether (PHAE) as described in U.S. Patent Publication No. US 2008/0014429 and polyetheramine nanocomposite barrier coatings as described in WO/2011/016838 and U.S. Provisional Patent Application 61/273,004. The contents of the above documents are hereby incorporated by reference as if recited in full herein.

As discussed above, the container body 10b can be a blow-molded body. Examples of blow-fill processes are described in U.S. Pat. Nos. 4,584,823, 4,995,519, 5,090,581, 5,356,052, 6,383,166, 6,860,405 and 7,028,862, the contents of which are hereby incorporated as if recited in full herein. However, other molding processes may be used. Although typically provided as a solid pre-formed stopper that is placed in an upper portion of the molded body, the stopper can be formed in situ in a respective mold (e.g., the top of the container body can be pinched together after filling with growth media and sensor material 14, 21, respectively, or molded to have an integral septum, not shown). If an integral septum is molded to the upper portion of the container body, it may be the same or a different material from the container body and may have increased thickness than the upstanding side wall of the container body.

The container 10 can be sterilized using conventional sterilization techniques, which is not limited to autoclaving such as, for example, one or more of gamma irradiation or ethylene oxide vapor hydrogen peroxide in lieu of or with autoclaving.

In some embodiments, two or more of the container body 10b, the gas barrier (e.g., silica) coating 35c and the top coating 45c can have similar thermal expansion coefficients which may ensure structural integrity (mechanical robustness) during the curing process or when exposed to high temperatures of autoclaving. The thermal expansion coefficients of the single layer container body 10b, the silica coating 35c and the top coating 45c can be similar so they do not delaminate during autoclaving.

In some particular embodiments, the gas barrier coating comprises a silica coating 35c and the silica coating 35c and top coating 45c can both be vapor deposited and be very thin, typically between 10 nm-10 micron thickness. For such thin film coatings, the thermal expansion coefficient mismatch may not matter.

The thermal expansion coefficient for polycarbonate (PC) is about 65-70×10-6/K, the silica coating is low 0.4-10x×10-6/K, the Parylene C has 35×10-6/K, carbon has 0.5-1.2×10-6/K. The coatings 35c, 45c can be inspected after autoclave to confirm the thermal expansion coefficients are compatible or suitable and adjustments made as appropriate. Currently, polycarbonate container bodies 10b have been coated with silica, then Parylene C. After autoclave, the coatings are intact as evaluated by visual inspection and by measuring the oxygen permeability.

Figure 5:
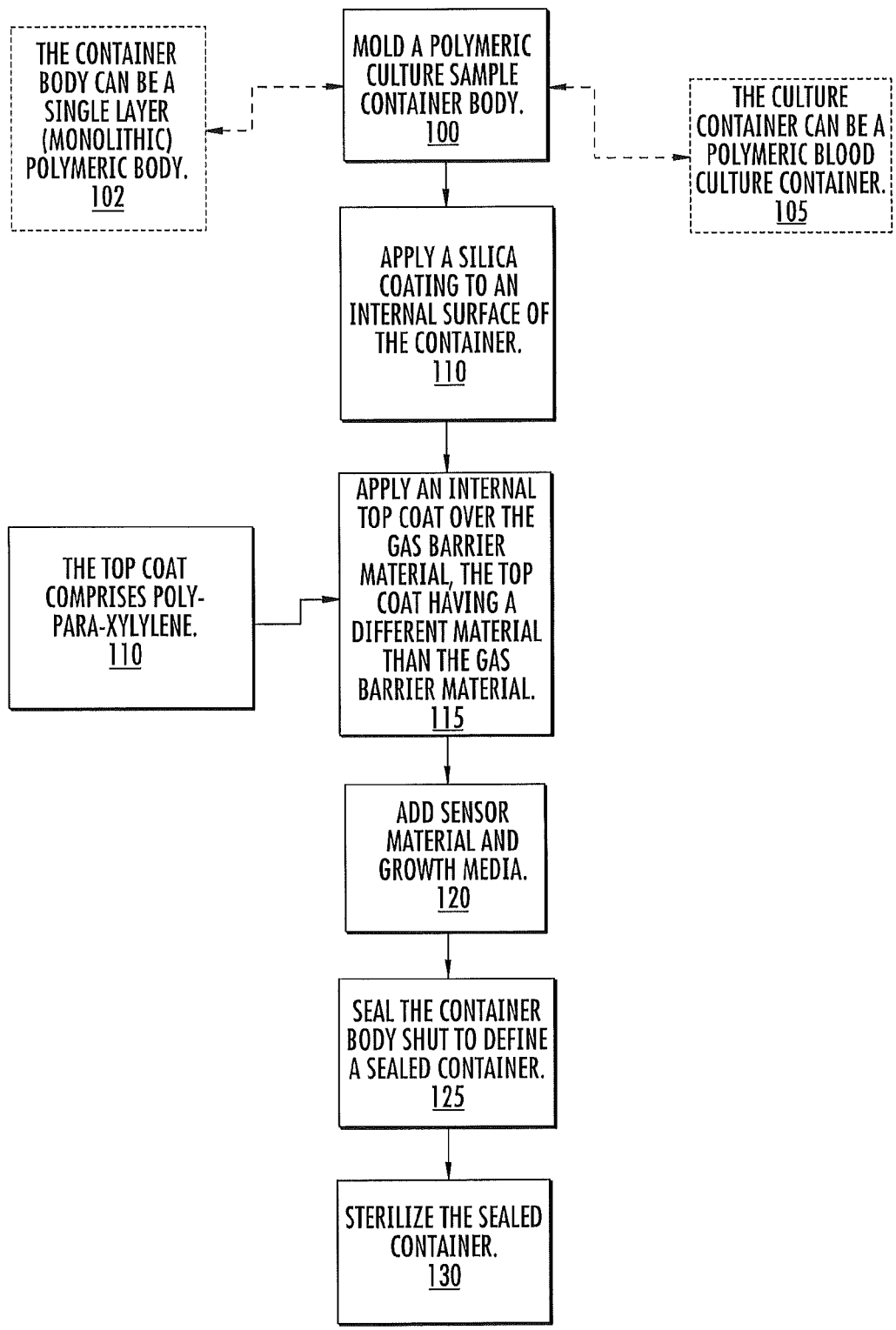
FIG. 5 is a flow chart of processing operations that can be used to carry out embodiments of the present invention.

FIG. 5 illustrates various process operations that can be used to fabricate culture sample containers according to embodiments of the present invention. A polymeric culture sample container body is molded (block 100). In a preferred embodiment, the molding can be carried out to produce a single layer (monolithic) container body (block 102). The sample container can be a blood sample culture container (block 105). An internal silica coating is applied to the container (block 110). An internal top coat is applied over the gas barrier material, the top coat having a different material than the gas barrier material (block 115). Sensor material and growth media can be added (block 110).

The container body can be sealed shut to define a sealed container (block 120). The sealed container is sterilized (block 130).

One of the exemplary uses of the containers 10 is in culturing a test sample to detect microbial growth in test sample (e.g., a blood sample). The method includes: (a) providing a specimen container 10 including a culture/growth medium 14 for promoting and/or enhancing growth of the microorganism; (b) introducing a test sample/specimen into the container; (c) incubating the specimen container the test sample (e.g., by placing the bottle in an incubation instrument); and (d) monitoring the specimen container for microorganism growth, either manually or automatically.

The present invention is explained in greater detail in the following non-limiting Examples.

EXAMPLES

Example 1

For this specific example, Sabic Lexan 124 polycarbonate (PC) or Topas cyclic olefin copolymer (COC) were used to manufacture the single layer plastic vials with the form of FIG. 1. The plastic vials were then coated internally and externally via vapor deposition with parylene C (Specialty Coating System). The oxygen transmission rates of the bare plastic vial, parylene coated, parylene coated and autoclaved (BacT/ALERT SN products, 121 C for at least 15 min with a heating ramp and cooling ramp) are compared here in Table 1.

TABLE 1

Oxygen Barrier for Parylene Coated Plastic Bottles

| Plastic | Vial Structure | Coating Thickness | Auto-clave | Oxygen Transmission Rate (cc/bottle/day/atm) |
|---|---|---|---|---|
| PC | Single layer | NA | No | 0.120 ± 0.0023 |
| PC | Single layer | 5 ± 1 μm | No | 0.109 |
| PC | Single layer | 10-15 μm | No | 0.087 |
| PC | Single layer | 5 ± 1 μm | Yes | 0.118 |
| PC | Single layer | 10-15 μm | Yes | 0.092 |
| COC | Single layer | NA | No | 0.068 ± 0.0003 |
| COC | Single layer | 5 ± 1 μm | No | 0.068 |
| COC | Single layer | 10-15 μm | No | 0.043 |
| COC | Single layer | 5 ± 1 μm | Yes | 0.070 |
| COC | Single layer | 10-15 μm | Yes | 0.046 |

As Table 1 shows, parylene by itself does not improve oxygen barrier at normal 5 μm thickness. It improves the oxygen barrier slightly at higher coating thickness, which is expensive and the oxygen barrier is not sufficiently good for cell culture products.

Example 2

Sabic Lexan 124 polycarbonate (PC) or Topas cyclic olefin copolymer (COC) were used to manufacture the plastic vials as described in Example 1. The plastic vials were then coated internally via vapor deposition with silica coating (KHS). Afterwards, the silica coated bottles were manufactured into BacT/ALERT FN Plus products by going through the sensor filling, dry oven curing, media filling, and autoclaving processes. Afterwards, the BacT/ALERT products manufactured using the silica coated bottles were placed in an accelerated chamber for accelerated aging study (80 C for 7 days). The oxygen transmission rates of the bare plastic vial, current multilayered BacT/ALERT products, silica coated bottle, BacT/ALERT bottles which went through the manufacturing process, and BacT/ALERT bottles which were accelerated aged were shown in Table 2 and compared here in FIG. 7. The results show that silica coating initially provides the gas barrier to monolayer polycarbonate vials comparable to that of multilayer bottles. However, after media fill and autoclave processes, the gas barrier provided by the silica coating significantly decreases. After accelerated aging, there were barely any gas barrier left from the silica coating. This phenomena might be because silica coating dissolves in non-acidic environments. The silica coating loss due to dissolution causes the oxygen barrier loss.

BacT/ALERT FN Plus products might cause faster silica dissolution than SN products under the current manufacturing process.

The data also shows that the Parylene moisture barrier top coat protected silica coating from dissolving and maintains the exceptional oxygen barrier of Silica coating when the bottles were filled, were autoclaved and were aged. Furthermore, even though Parylene coating by itself did not improve the bottle's oxygen barrier, when added on top of silica coating, unexpectedly, the Parylene coating further improved the oxygen barrier of the silica coated bottles, decreasing the oxygen transmission rate almost a magnitude more when coated at 10 micron thickness.

TABLE 2

Oxygen Barrier of Silica Coated Bottles - BacT/ALERT FN Plus Products
(OTR unit: cc/package/day/atm)
Summary

| Material | Raw bottle OTR | OTR - Fresh Silica Coated | OTR - Silca coated After Manufacturing | OTR - After Shaking | OTR - After 80 C. Accelerated | OTR - After 80 C. Accelerated & Shaking |
|---|---|---|---|---|---|---|
| PC | 0.12 | 0.0040 | 0.0400 | 0.0480 | 0.1110 | 0.0960 |
| COC | 0.068 | 0.0007 | 0.0070 | 0.0180 | 0.0440 | 0.0515 |
| Multilayer | 0.003 | | 0.0041 | | | 0.0034 |

Example 3

Sabic Lexan 124 polycarbonate (PC) were used to manufacture the plastic vials as described in Example 1. The plastic vials were then coated internally via vapor deposition with silica coating (MIS) as described in Example 2. Afterwards, these silica coated plastic vials were sent to Specialty Coating Systems for Parylene C coating. Specialty Coating Systems coated internal and external surfaces of these bottles with Parylene C having two levels of coating thickness (average 5 micron and 10 micron). The coated bottles were then manufactured into BacT/ALERT SN products and accelerated aged as described in Example 2. The oxygen transmission rates of the SN products manufactured from current multilayered bottles and from the Silica/Parylene coated bottles, and the SN products after accelerated aging process were tested. The data are shown in Table 3 and illustrated in FIG. 6.

The OTR data confirms that silica coated bottles without any extra coating protection (OTR of 0.004 cc/package/day/atm) lost its oxygen barrier after being filled and subjected to the manufacturing process under heat and steam conditions (OTR of 0.0131 cc/package/day/atm). The oxygen barrier provided by the silica coating was further lost after aging process (OTR of 0.0861 cc/package/day/atm). The extra oxygen barrier provided by the silica coating was almost all lost after accelerated aging process. These indicated that the silica coating might be dissolved under the media with these processes. Notice that there is slight difference on OTR data between silica coated bottle after manufacturing in Table 3 (0.0131 cc/package/day/atm) and silica coated after manufacturing in Table 2 (0.04 cc/package/day/atm). The difference might be due to the different media for different BacT/ALERT products. The media in

TABLE 3

Oxygen Barrier of Silica/Parylene Coated
Bottles - BacT/ALERT SN Products

| Bottle Material | Bottle OTR After Manufacturing (cc/package/day/atm) | Bottle OTR After 80 C. accelerated aging (cc/package/day/atm) |
|---|---|---|
| Multilayer | 0.0028 | 0.0022 |
| PC/silica coated | 0.0131 | 0.0861 |
| PC/silica coated, SCS 5 um | 0.0037 | 0.0035 |
| PC/silica coated, SCS 10 um | 0.0006 | 0.0004 |

Note:
the OTR for PC monolayer bottle is 0.120 and the OTR for silica coated empty PC bottle is 0.004 cc/package/day/atm.

The foregoing is illustrative of embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A container for culturing a test sample, comprising:
   a molded monolithic single layer polymeric container body having an upwardly extending, visually transmissive wall with an inner surface and a wall thickness that is between about 0.2 mm and 10 mm;
   a thin gas barrier coating having a thickness between about 1 nm and 1000 microns comprising silica on the inner surface of the container body, wherein the gas barrier coating is visually transmissive;

an internal top coating directly on the gas barrier coating, wherein the internal top coating is visually transmissive and the internal top coating is selected from the group consisting of a polyester, polyvinylidene chloride (PVDC), polyvinyl alcohol (PVOH), poly(acrylonitrile) (PAN), polyamide (PA), a polyurethane, an acrylic polymer, a polyetheramine, a metal oxide, a polypropylene film with reprocessed/recycled polyhydroxyamino ether (PHAE), a poly-para-xylylene polymer, acetylene, and any combination thereof; and a cap sealably attached to the container body to define a sealed container, wherein the sealed container has an oxygen transmission rate (OTR) after exposure to 121 degrees C. for 15 minutes and throughout a one year shelf life that is between about 0.0001-0.04 (cc/package/day/atm, measured at 20 degrees C., 40% RH), and wherein the container body has only two inner coating layers, the gas barrier coating as a first inner coating layer and the internal top coating as a second inner coating layer.

2. The container of claim 1, further comprising an LES sensor on the internal top coating in a bottom of the container body, and cell culture media in the container, wherein the internal top coating is configured to keep the gas barrier coating from contacting and/or chemically interacting with contents of the sealed container to thereby keep the gas barrier intact in a non-acidic environment, and wherein the thin gas barrier coating is a better gas barrier than the internal top coating.

3. The container of claim 1, further comprising an external coating on the container body, the external coating comprising a material corresponding to the internal top coating.

4. The container of claim 1, wherein the internal top coating comprises poly-para-xylylene.

5. The container of claim 1, wherein the internal top coating comprises carbon.

6. The container of claim 1, wherein the internal top coating is acetylene.

7. The container of claim 1, wherein the container body has a wall thickness of between 1-5 mm, the gas barrier coating has a thickness of between 10 nm to 1000 nm and the internal top coating has a thickness of between 10 nm to 50 microns.

8. The container of claim 1, wherein the container body has a wall thickness that is between 1-2 mm, and wherein the gas barrier coating has a thickness of between 10 nm to 100 nm and the internal top coating has a thickness of between 10 nm to 1 micron.

9. The container of claim 1, wherein the container body is a transparent polycarbonate body or a transparent cyclic olefin copolymer body.

10. The container of claim 1, wherein the container body is devoid of an external coating.

11. The container of claim 1, wherein the OTR after one year is between 0.0001 and 0.01 (cc/package/day/atm).

12. The container of claim 1, wherein the internal top coating prevents silica from the thin gas coating barrier from being present at an internal surface of the container after the exposure to 121 degrees C. for 15 minutes and throughout the one year shelf life.

13. A container for culturing a test sample, comprising:
a molded monolithic single layer polymeric container body having an upwardly extending, visually transmissive wall with an inner surface and a wall thickness that is between 0.2 mm and 10 mm;

a thin gas barrier coating having a thickness between about 1 nm and 1000 microns comprising silica on the inner surface of the container body, wherein the gas barrier coating is visually transmissive;

an internal top coating directly on the gas barrier coating, wherein the internal top coating is visually transmissive and the internal top coating is selected from the group consisting of a polyester, polyvinylidene chloride (PVDC), polyvinyl alcohol (PVOH), poly(acrylonitrile) (PAN), polyamide (PA), a polyurethane, an acrylic polymer, a polyetheramine, a metal oxide, a polypropylene film with reprocessed/recycled polyhydroxyamino ether (PHAE), a poly-para-xylylene polymer, acetylene, and any combination thereof; and a cap sealably attached to the container body to define a sealed container, wherein the sealed container has an oxygen transmission rate (OTR) after the polymeric container body with the thin gas barrier coating and the internal top coating have been exposed to 121 degrees C. for 15 minutes and throughout a one year shelf life that is between 0.0001 to 0.01 (cc/package/day/atm, measured at 20 degrees C., 40% RH), wherein the container body has only two inner coating layers, the gas barrier coating as a first inner coating layer and the internal top coating as a second inner coating layer.

14. The container of claim 13, wherein the internal top coating prevents silica from the thin gas coating barrier from being present at an internal surface of the container after the exposure to 121 degrees C. for 15 minutes and throughout the one year shelf life.

15. A container for culturing a test sample, comprising:
a molded monolithic single layer polymeric container body having an upwardly extending, visually transmissive wall with an inner surface and a wall thickness that is between about 1 mm and about 2 mm with sufficient rigidity to have a self-supported tubular shape with a height that is greater than a width thereof;

a thin gas barrier coating having a thickness of between about 10 nm and 1000 nm comprising silica directly on the inner surface of the container body, wherein the gas barrier coating is visually transmissive;

an internal top coating having a thickness of between about 10 nm to about 1 micron directly on the gas barrier coating, wherein the internal top coating is visually transmissive and the internal top coating is selected from the group consisting of a polyester, polyvinylidene chloride (PVDC), polyvinyl alcohol (PVOH), poly(acrylonitrile) (PAN), polyamide (PA), a polyurethane, an acrylic polymer, a polyetheramine, a metal oxide, a polypropylene film with reprocessed/recycled polyhydroxyamino ether (PHAE), a poly-para-xylylene polymer, acetylene, and any combination thereof, and wherein the container body has only two inner coating layers, the gas barrier coating as a first inner coating layer and the internal top coating as a second inner coating layer; and a cap sealably attached to the container body to define a sealed container, wherein the cap on the container body encloses a colorimetric sensor and non-acidic cell culture media, wherein the sealed container, post sterilization, has an oxygen transmission rate (OTR), measured after accelerated aging at 80 degrees C. for seven days, that is between 0.0001-0.03 (cc/package/day/atm, measured at 20 degrees C., 40% RH).

16. The container of claim 15, wherein the internal top coating prevents silica from the thin gas coating barrier from being present at an internal surface of the container after the accelerated aging at 80 degrees C. for seven days.

17. A container for culturing a test sample, comprising:
- a molded monolithic single layer polymeric container body having an upwardly extending, visually transmissive wall with an inner surface and a wall thickness that is between about 0.2 mm and 10 mm;
- a thin gas barrier coating having a thickness between about 1 nm and 1000 microns comprising silica on the inner surface of the container body, wherein the gas barrier coating is visually transmissive;
- an internal top coating directly on the gas barrier coating, wherein the internal top coating is visually transmissive and does not include silica; and
- a cap sealably attached to the container body to define a sealed container,
- wherein the sealed container has an oxygen transmission rate (OTR) after exposure to 121 degrees C. for 15 minutes and throughout a one year shelf life that is between about 0.0001-0.04 (cc/package/day/atm, measured at 20 degrees C., 40% RH),
- wherein the container body has only two inner coating layers, the gas barrier coating as a first inner coating layer and the internal top coating as a second inner coating layer.

18. The container of claim 17, wherein the internal top coating prevents silica from the thin gas coating barrier from being present at an internal surface of the container after exposure to 121 degrees C. for 15 minutes and throughout the one year shelf life.

* * * * *

UNITED STATES PATENT AND TRADEMARK OFFICE
CERTIFICATE OF CORRECTION

PATENT NO. : 9,523,110 B2
APPLICATION NO. : 13/789940
DATED : December 20, 2016
INVENTOR(S) : Wolters et al.

Page 1 of 1

It is certified that error appears in the above-identified patent and that said Letters Patent is hereby corrected as shown below:

In the Specification
Column 15, Line 36: Please correct "(MIS)" to read -- (KHS) --

Signed and Sealed this
Sixth Day of June, 2017

Michelle K. Lee
*Director of the United States Patent and Trademark Office*